United States Patent [19]

Teinturier

[11] 4,385,405
[45] May 31, 1983

[54] HIP PROSTHESIS AND ITS METHOD OF FITTING

[76] Inventor: Pierre L. Teinturier, Champeaux, 63110 Beaumont, France

[21] Appl. No.: 193,316

[22] Filed: Oct. 2, 1980

[30] Foreign Application Priority Data

Oct. 3, 1979 [FR] France .............................. 79 24589

[51] Int. Cl.³ .............................................. A61F 1/04
[52] U.S. Cl. ..................................... 3/1.912; 3/1.913; 128/92 C; 128/92 CA
[58] Field of Search ................... 3/1.912, 1.913, 1.91; 128/92 C, 92 CA

[56] References Cited

U.S. PATENT DOCUMENTS

| | | | |
|---|---|---|---|
| 2,910,970 | 11/1959 | Urist | 3/1.9 R X |
| 3,713,860 | 1/1973 | Auskern | 3/1.9 X |
| 3,829,904 | 8/1974 | Ling et al. | 3/1.912 |
| 3,846,846 | 11/1974 | Fischer | 3/1.913 |
| 3,871,031 | 3/1975 | Boutin | 3/1 X |
| 3,896,505 | 7/1975 | Timmermans | 3/1.913 |
| 3,924,275 | 12/1975 | Heimke et al. | 3/1.912 |
| 3,977,026 | 8/1976 | Battault | 3/1.911 |
| 4,180,873 | 1/1980 | Fixel | 3/1.912 |
| 4,262,369 | 4/1981 | Roux | 3/1.912 |

FOREIGN PATENT DOCUMENTS

| | | | |
|---|---|---|---|
| 2416004 | 8/1979 | France | 3/1.912 |
| 1302834 | 9/1971 | United Kingdom | 3/1.912 |

Primary Examiner—Richard J. Apley
Assistant Examiner—David J. Isabella
Attorney, Agent, or Firm—Sughrue, Mion, Zinn, Macpeak and Seas

[57] ABSTRACT

A prosthetic socket 1 is made in a generally crescent shape with an outer cylindrical surface and includes horns 5, 6 which may be contracted, in order to allow it to be introduced, in the manner of a clip, in a cylindrical osseous cavity, where it is held by elasticity, without any cementing. The anchorage of this type of prosthesis is made directly onto the bone, using materials with a Young's modulus very close to the Young's modulus of the spongiosa tissue of the pelvis guarantees longevity of the anchorage, which is protected from loosening which may occur when cements of the methyl methacrylate type or others are used, such as metal or ceramic materials designed to be self-fixing, but of which the Young's modulus is sufficiently different from the Young's modulus of the bone that mechanical stresses may occur causing loosening. The invention also relates to an artificial head of a femur of three part construction.

5 Claims, 8 Drawing Figures

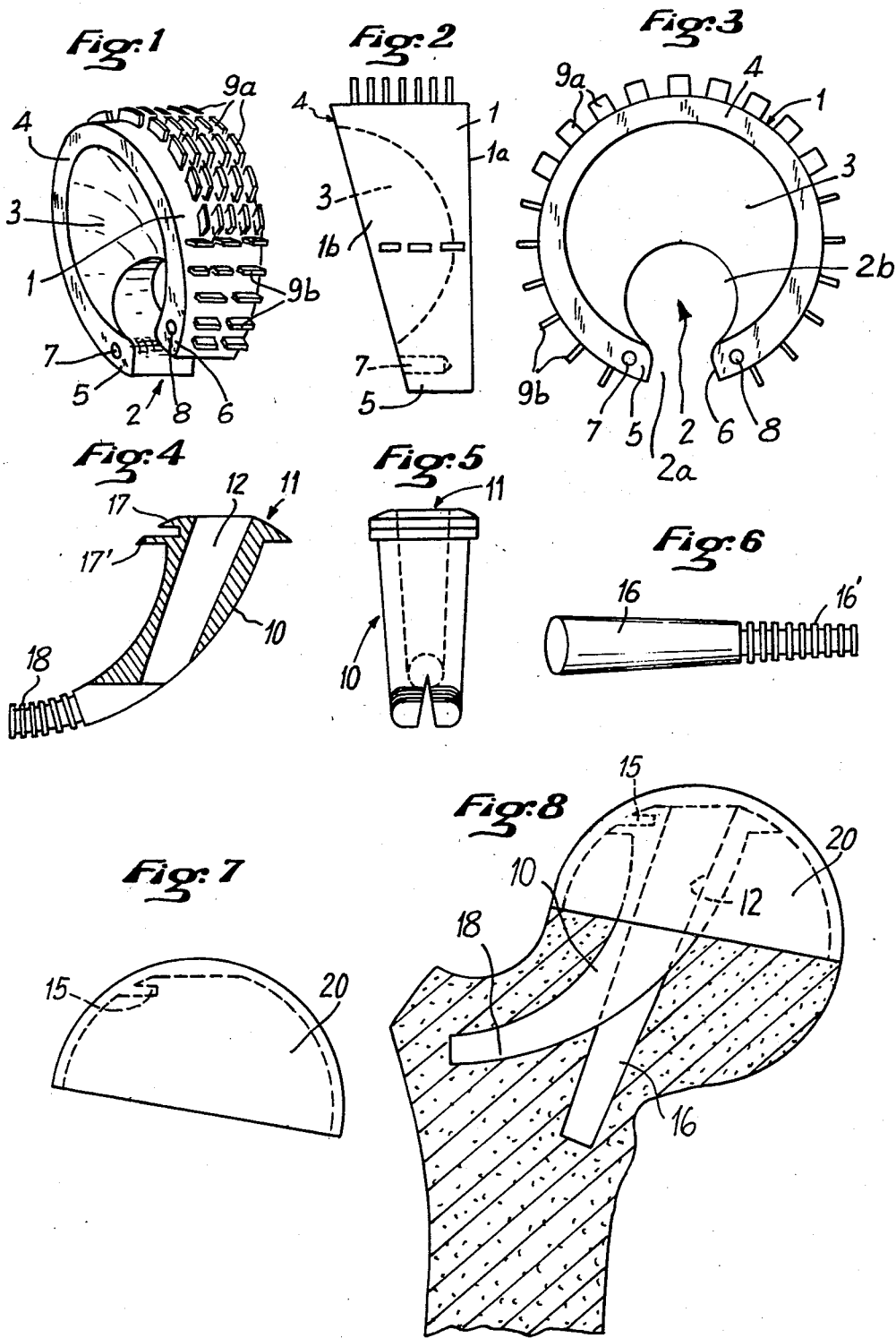

HIP PROSTHESIS AND ITS METHOD OF FITTING

FIELD OF THE INVENTION

The present invention relates to a hip prosthesis forming a joint for the head of the femur onto the pelvis. The prosthesis comprises a prosthetic cotyloidal element and a femoral element; the cotyloidal element is provided in order to replace the damaged cotyloidal cavity of the pelvis. The femoral element makes it possible to re-constitute a spherical femoral head which is adapted to the cotyloidal element. Its fitting in place and the equipment necessary for this also form part of this invention.

BACKGROUND OF THE INVENTION

Until now, hip prostheses have included a cotyloidal element positioned in the cotyloidal cavity of the pelvis; and fixing of the element to the pelvis bone being ensured both using cement of the methyl methacrylate type, and making use of irregularity of the surface in contact with the bone, the irregularity being brought about using a range of processes (small cuts, pitting, scores and so on). The disadvantage of these processes lies in the fact that neither methyl methacrylate nor the materials used to obtain a bond in the pelvic cavity has the same Young's modulus (elastic modulus) as the spongy tissue of the pelvis. The principle of selffixing of the present invention is based on the proximity of the Young's modulus of the prosthesis to that of the spongy tissue of the pelvis, making it possible to have two materials next to each other which are compatible.

The same problem arises with regard to the femoral prosthesis where attachment of the prosthesis in the medullary canal of the bone is provided using either, as was the case for the pelvis, methyl methacrylate which compensates for the lack of match between the tail of the femoral prosthesis and the diameter of the medullar cavity, or by using a metal prosthesis with a larger diameter and having, as was the case for the pelvis, irregularities intended for correct fixing of the bone onto these irregularities.

Here, too, the difference in the Young's modulus which exists between steel and methyl methacrylate on the one hand, and the cortical bone of the femur on the other, is such that under the effect of mechanical stresses, loosening occurs leading to the need for further complete surgical work.

The femoral prosthesis concerned in this invention is intended to be fixed not in the medullar cavity but in the spongy tissue of the femoral head and neck, by using a material of which the Young's modulus is close to that of the spongy tissue (high density polyethylene).

Two small tongues in polyethylene are introduced into the spongy tissue and, owing to their elasticity, become engaged with this spongy tissue so that an osseous growth is able to form around these tongues in polyethylene and provides longterm attachment of the prosthetic elements.

At the pelvis end, additional attachment is provided using clips so that a dynamic connection is made between the cotyloidal element and the cavity which receives it.

The description which follows, with reference to the attached drawings, given only by way of example, will fully explain how the invention may be carried out.

BRIEF DESCRIPTION OF THE FIGURES

FIG. 1 is a perspective view of a cotyloidal element according to the invention;

FIG. 2 is a side elevational view of the element in FIG. 1 with a majority of tongues projecting from the outer surface purposely deleted;

FIG. 3 is a view in front elevation of the same element;

FIG. 4 is a cross-sectional view of an upper anchor of a femoral prosthesis;

FIG. 5 is a view at 90° to that of the preceeding figure;

FIG. 6 is a side view of a lower anchorage for the femoral prosthesis

FIG. 7 shows a cup-shaped element for this prosthesis, and;

FIG. 8 shows the assembly of elements of FIGS. 4, 6 and 7, with the femoral prosthesis partly in cross section.

DESCRIPTION OF THE PREFERRED EMBODIMENT

The device described below comprises elements of a hip prosthesis the implantation of which requires no cement of the methyl methacrylate type or similar materials. It has two parts:

a cotyloidal element a femoral element

The Cotyloidal Element

The prosthetic socket made of high density polyethylene or other synthetic material (polyethylene incorporating, in particular, molybdenum bisulphide) is fashioned in such a way that its fitting to the patient ensures direct osseous attachment without the use of cement.

The prosthetic socket 1 is made up of a cylindrical component terminating in the axial sense at two planes, one of which, the posterior or internal plane 1b, is normal to the axis of revolution of the cylindrical component socket 1 and the other, the anterior plane, may form an angle of approximately 15° with the normal for the axis. Viewed axially (FIG. 3), the socket has an overall circular exterior profile, and has an indentation 2, formed by a radial slot 2a terminating in a cylindrical opening 2b whose axis is offset both parallel to the axis of the cylindrical socket 1, the socket thus having the appearance of a horseshoe when viewed at this angle.

A spherical cavity 3 is machined (or formed in some other manner) in the anterior face, forming a seating for a spherical joint. A plane portion 4 having a lateral face 1b may be left around the cavity. In the edges 5,6 or horns, of the socket 1 at the indentation 2 two holes 7,8 are provided for the location of a tool used for closing the socket indentation 2 in the manner of a clip. In order to place the socket in the pelvis of the patient, a cylindrical cavity of appropriate dimensions is hollowed out in the bone of the pelvis, at the place of the damaged joint which is to be replaced. The dimensions of the cylinder in the bone correspond to those of the socket, so that the latter can be maintained there elastically after being driven in whilst it is held in place.

In order to facilitate attachment of the socket, in addition to the clip action which maintains the periphery of the socket against the bone, the provision of the flexible tongues 9a,9b polyethylene ensures long-term osseous attachment to these tongues, in view of the fact that the material used (high density polyethylene) has a Young's modulus close to that of the cotyloidal bone, and modifications in the shape of the socket which occur at each step will be transmitted by* the prosthesis in a harmonious way to the spongiosa of the bone material surrounding the prosthesis. These tongues 9a, 9b which are between 0.5 and 2 mm thick and 2-3 mm high, are arranged in rows, separated from one another either by several millimeters or by a simple cut of narrower gap.

*added to correct, presumably faulty, French text (Translator's note) cotyloidal joint.

The spatial arrangement of these tongues enables them to be divided into 2 groups:
 an upper group
 a lower group The upper group occupies the upper half or third of the periphery of the socket. It consists of tongues 9a arranged in planes parallel to the medial plane of the prosthetic component. Intra-osseous locking of these tongues is designed to stabilise the prosthetic socket in the frontal plane.

The lower group occupies the forward third or quarter and the rearward third or quarter of the periphery of the socket. It consists of tongues 9b arranged orthogonally with respect to the tongues of the upper group, i.e. tongues 9b are in planes passing through the axis of the cotyloidal joint (radial planes).

This arrangement off the tongues is used for positioning the socket in the osseous cylinder. First bearing tongues 9b is introduced into the osseous cylinder, when the two edges 5 and 6 are brought together by means of an appropriate tool, such as a clamp driven into holes 7 and 8. This is why the lower tongues are arranged in planes passing through the axis of the cylinder forming the socket. Once the lower part is engaged in the bottom of the osseous cylinder, the upper part bearing tongues 9a can be tilted by pivoting it on the bearing surface of the lower part. The upper tongues 9b, are thus able to flex when passing against the cylindrical part of the osseous cavity.

In order to allow the anteior and posterior horns of the prosthetic socket to follow the movements of the pelvic joint, the upper part of the cotyloidal component can be provided with modifications of shape in the form of indentations or changes in thickness, designed to thin down the bottom or roof of the said socket; the size, shape and number of these indentations varying according to the material used, its Young's modulus, the diameter of the socket, and the thickness of the roof of the socket.

After fitting in place of the cotyloidal prosthesis, the tongues resume their initial position due to their elasticity; the bone reforming around these tongues ensuring a good connection between the bone and the prosthetic element.

locking in place of the prosthesis is thus ensured:
(1) in the frontal plane, by the upper tongues 9a;
(2) in the saggital plane, by the tongues 9b of the two lower groups;
(3) in the horizontal plane, by producing the cylinder of the prosthetic joint in the form of a segment which engages as a force fit in the segment of the osseous cylinder, hollowed in the pelvis.

Positioning of the prosthetic joint is done using a clamping process in which, by drawing the horns together, first the lower part of the prosthesis contracted by the drawing together of the horns is introduced and then the upper part with the upper tongues is engaged in the osseous cylinder. After penetration of the prosthetic element into the osseous cylinder, the clamp is opened, allowing, owing to the elasticity of the material, the periphery of the socket to be forcibly applied onto the bone.

The diameter of the spherical segment, designed to receive the prosthetic head of femur is a function of the type of femoral prosthesis used which may be:
 either a prosthesis with a medullar shaft which may or may not be fixed with cement; the diameter of manufacture of the socket than corresponding to the type of femoral prosthesis used;
 or the femoral prosthesis described below, known as an anchored cup.

The anchored cup has three separate parts:
(1) The upper anchor 10 (FIGS. 4 and 5)
(2) The lower anchor 16 (FIG. 6)
(3) The cup 20 (FIG. 7)

(1) The upper anchor made of high density polyethylene includes in a single part 10, a platform 11 for abutment against the femoral head. This ovoid-shaped platform corresponds to the segment of the resected* femoral head at the upper part of the femoral sphere. The upper part of the femur is shown in hatched lines in FIG. 8. The cup is fixed onto this platform mechanically either by using small pins forming a

*There is presumably an error in the Frency text here (Translator's note) tight frictional fit, or by forming a hollow shape in the bone face of the cup which is adapted to the platform and formed either by microfusion or by machining.

This platform has an opening (12) through which the lower anchor 16 (FIG. 6) passes.

The platform is extended by the upper anchor 18 which follows the upper edge of the femoral neck (FIG. 8). It consists of a polyethylene shank of decreasing diameter, its surface being provided with tongues 18 in polyethylene arranged according to the various diameters of the shank. The distal part of this upper anchor is forked, and provided with a space between the two elements of this forking. At this forking the polyethylene tongues are arranged over a half-diameter, so that the drawing together of two shank halves of the forking makes up a complete circular arrangement of the tongues.

Positioning of this upper anchor requires:
 a re-constructed model of the femoral head
 a drilling device
 the forking, during fitting of the upper anchor is eliminated by drawing together, using ligatures of readsorbable thread, of the two shank halves forming the distal forking. The reabsorption of the thread will allow return of the initial bifidity as a result of the elasticity of the material, providing attachment under force in the horizontal plane of the distal part of this upper anchor.

2. The lower anchor is a polyethylene shank 16 also provided with tongues 16' arranged as previously over successive diameters of the polyethylene shank and spaced several millimeters apart. With their diameter decreasing from top to bottom, these two shanks pass through the opening in the platform of the upper anchor and rest against the internal tissue and the neighbouring spongy tissue (FIG. 8). The two anchors thus work by traction for the upper anchor and by compression for the lower anchor.

3. The cup is of metal or made of a synthetic material compatible with theprosthetic socket. It represents a segment occupying approximately two-thirds of a sphere.

At its upper part, it is machined so as to be hollow, which enables it to adapt to the shape of the platform, a peripheral catch engages with the external edge of the platform and prevents rocking movements cup causing it to turn inwards. The edges of the platform stabilise the cup in the saggital plane. The outer diameter of the cup corresponds to the inside diameter of the cotyloidal prosthesis chosen, or of the socket, if no cotyloidal prosthesis is used. The size of the anchorages is selected as a function of the femoral epiphysis in question, several sizes are thus necessary by reason of the morphology of the patient.

The osseous face of the cup will be formed in an irregular manner in order to encourage complementary stabilisation as a result of growth of osseous tissue.

Fitting of the prosthesis is carried out in the following way:
- (a) location of the axis of the femoral collar
- (b) formation of a spherical shaping in the femoral head using a hollow cutter of suitable diameter
- (c) positioning of a reconstructed model allowing cutting of the upper end of the femoral head.

Using this model, the path for the upper anchorage is formed, and when the upper anchor is in place, the lower anchorage is put in place through the platform.

Finally, the cup is secured onto the platform and the remainder of the femoral head.

I claim:

1. A hip prosthesis for replacing a hip joint by fitting a prothesis into a formed cylindrical bore cavity in the pelvis bone, said prothesis comprising:
a horseshoe shaped cotyloidal element (1) made of an elastically deformable material comprising a generally outer cylindrical surface, said cotyloidal element having a longitudinal axis and being delimited by two end faces, said end faces comprising a first end face being substantially perpendicular to the axis of the cylindrical surface, and a second end face being oblique with regard to said longitudinal axis, said end faces forming on the cylindrical surface a longer side and a shorter side, said oblique surface having formed therein a cavity in the form of a spherical cup, and said outer cylindrical surface being cut out on the shorter side to form an indentation (2) defining horns on respective sides of the cut out allowing the perimeter of the element to be reduced by drawing together the horns (5, 6) formed by the indentation;
whereby, the horseshoe shaped cotyloidal element may be deformed elastically in order to reduce its diameter to permit it to be engaged into the bore cavity, after which the cotyloidal element is released so as to take its initial shape to elastically clamp said element into the bore cavity.

2. The prosthesis as claimed in claim 1, wherein holes (7, 8) are provided within the end faces of said horns in order to draw the sides of the cotyloidal element together at the indentation.

3. The prosthesis as claimed in claim 2, wherein the outer cylindrical surface of the cotyloidal element (1) is furnished with radially outwardly projecting flexible flat tongues, said tongues including first tongues (9a) disposed on the surface thereof opposite to the indentation (2) and positioned in planes parallel to the first end face and second tongues (9b) disposed on the sides of the horns and being positioned in planes passing through the longitudinal axis of the cylindrical surface.

4. The prosthesis as claimed in claim 1, further including a prosthetic femoral cup, said femoral cup comprising an upper anchor made of an elastically deformable material, said upper anchor comprising a platform (11) and an integral, elongated hooked shank (10) dependent therefrom, and wherein said platform and said shank include a straight conical passage passing through said platform and the side of said hooked shank, a lower anchor (16) configured to and mounted within said conical passage and having a portion extending axially beyond said passage and to the side of said shank (10) at the end remote from the plaform such that said lower anchor (16) and said end of said shank (10) form an angle therebetween, and wherein said end of the anchor shank remote from the platform is split longitudinally to form laterally separated parts which are slightly divergent when unflexed.

5. A method for positioning a hip prosthesis comprising a cylindrical cotyloidal element made of an elastically deformable material bearing small diameter indentations within the outer cylindrical surface thereof to form an element of horseshoe shape, thereby allowing the perimeter diameter to be reduced, said method comprising:
boring a cylindrical cavity within the pelvis bone whose cavity diameter is less than the outer diameter of the cylindrical element,
compressing the horseshoe shaped cylindrical cotyloidal element together by deforming the element elastically in order to reduce its diameter,
engaging the cotyloidal element into the bored cavity of the pelvis bone, and
releasing the elastically deformed cylindrical element to permit it to retain its initial shape such that it is elastically clamped into the bored cavity.

* * * * *